(12) United States Patent
Davis et al.

(10) Patent No.: US 8,852,092 B1
(45) Date of Patent: Oct. 7, 2014

(54) EYELID ENGAGING EYEWEAR

(76) Inventors: Mardy Davis, Wilmington, NC (US);
Joyce Rivera, Newark, NJ (US)

( * ) Notice: Subject to any disclaimer, the term of this patent is extended or adjusted under 35 U.S.C. 154(b) by 60 days.

(21) Appl. No.: 13/494,171

(22) Filed: Jun. 12, 2012

(51) Int. Cl.
*A61B 1/32* (2006.01)

(52) U.S. Cl.
USPC .......................................................... 600/236

(58) Field of Classification Search
USPC ........ 600/236, 244, 235; 351/57, 59; 294/1.2; 606/107
See application file for complete search history.

(56) References Cited

U.S. PATENT DOCUMENTS

| | | | | |
|---|---|---|---|---|
| 4,126,345 A | * | 11/1978 | List | 294/1.2 |
| 4,326,742 A | * | 4/1982 | Ingram | 294/1.2 |
| 4,740,069 A | * | 4/1988 | Baum | 351/57 |
| 4,837,862 A | * | 6/1989 | Heil | 2/12 |
| 5,050,918 A | * | 9/1991 | Kolze | 294/1.2 |
| 6,544,169 B2 | * | 4/2003 | Putrino et al. | 600/236 |
| 7,011,403 B1 | * | 3/2006 | Pacheco | 351/59 |
| 7,101,038 B2 | * | 9/2006 | Miceli | 351/59 |
| 7,985,180 B2 | * | 7/2011 | Brown | 600/236 |

\* cited by examiner

*Primary Examiner* — Mary Hoffman
*Assistant Examiner* — Tara Carter

(57) ABSTRACT

The eyelid-engaging eyewear is comprised of an eyewear frame having open spaces in front of the eyes and through which eyelid engaging means attach to and pivot. The eyelid engaging means include armatures at distal ends, which engage eyelids of an end user and lift and hold up said eyelids in order to assist in installing and/or removing contact lenses from the eyes of the end user. The eyewear frame includes a centrally located suction cup that is directed inwardly and adheres to the forehead of the end user so as to secure the device to the end user. The eyewear is worn in a normal fashion, and upon rotation of the eyelid engaging means shall lift and hold up said eyelids of the end user.

3 Claims, 3 Drawing Sheets

EYELID ENGAGING EYEWEAR

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of eyewear, more specifically, eyewear uniquely capable of engaging and holding an eyelid in an up position while installing/removing contact lens from either eye.

Contact lenses have been around for quite some time and significantly help with problems associated with vision. However, installing and removing contact lenses from the eye can be problematic as the surface of the eye is quite sensitive. In times requiring installing or removing contact lenses, new wearers may find it difficult to keep eyelids from interfering. In said situation, it is desirable to have an eyelid engaging means that aids in lifting and holding eyelids up so as to accommodate installation and/or removal of contact lenses.

The device of the present application seeks to address this secure itself to the face of the end user, and which includes eyelid engaging means therein.

B. Discussion of the Prior Art

As will be discussed immediately below, prior art discloses eyewear in which eyelid engaging means are integrated therein, and which rotate with respect to the eyewear in order to engage and lift eyelid's of an end user in order to hold open an eye for installation and/or removal of contact lens with respect to said eye(s); wherein the eyelid engaging eyewear includes an eyewear frame with open spaces in front Of the eyes; wherein the eyewear frame includes a suction cup that is centrally located on the eyewear frame and directed inwardly so as to engage forehead skin of an end user in order to secure said eyewear frame there against; wherein the eyelid engaging means attaches to and pivots about a pair of pivot points provided on the eyewear frame; wherein the eyelid engaging means includes armatures that extend laterally at each distal end and which engage eyelids of the end user, and upon rotation of the eyelid engaging means shall lift and hold up the eyelid for use when installing and/or removing contact lens with respect to the eyes of the end user.

The Ingram Patent (U.S. Pat. No. 4,326,742) discloses a method and apparatus for inserting and removing soft contact lens, which includes a frame that is worn somewhat like conventional eyeglasses but with open spaces in the front of the eyes so that the contact lens may be readily positioned directly in front of the center of the eye and the lens moved into engagement with the surface of the eye in a gently but effective manner. However, the apparatus does not include eyelid engaging means that rotate inwardly with respect to the eyewear frame to engage eyelids of an end user, and which lift and hold up said eyelids so as to enable installation and/or removal of contact lenses.

The Renard et al. Patent (U.S. Pat. No. 7,478,850) discloses an ocular device to facilitate the positioning and insertion of an object onto a subject's eyes having a base comprising a mouthpiece and at least one support coupled to the base. However, the device requires an end user to bite on a mouthpiece, and is not eyewear that is placed on the face of an end user in a manner consistent with eyeglasses, and from which eyelid engaging means are manipulated thereon to engage and hold up eyelids for use in installing and/or removing contact lenses there from.

The List Patent (U.S. Pat. No. 4,126,345) discloses a device for handling soft contact lenses comprising a pair of resilient pincer arms. However, the device does not resemble eyewear that is worn like eyeglasses and which includes eyelid engaging means therein.

The Py Patent (U.S. Pat. No. 6,739,636) discloses a contact lens applicator and cartridge use in connection there with. Again, the applicator and cartridge is not eyewear that is worn like eyeglasses, and which includes eyelid engaging means therein.

The Tano Patent (U.S. Pat. No. 7,666,190) discloses a holder of contact lens for vitreous body operation, and holding part and connection part of contact lens for vitreous body operation. Again, the holder is not eyewear that is worn like eyeglasses, and which includes eyelid engaging means therein.

The Ranani Patent (U.S. Pat. No. 4,703,964) discloses a tinted contact lens fitter having a scissors-type support. However, the contact lens fitter is a scissor-like device that is manually held by hands, and not eyewear worn on a face of an end user.

The Putrino et al. Patent (U.S. Pat. No. 6,544,169) discloses an eyelid retraction device. Again, the device is a hand-held device that is not worn on a face like a pair of eyeglasses.

The Harbert Patent (U.S. Pat. No. De's. 428,041) illustrates an ornamental design for a contact lens applicator and remover, which does not resemble eyewear having eyelid engaging means integrated therein.

The Allendorf et al. Patent (U.S. Pat. No. Des. 321,355) illustrates an ornamental design for a combined eyeglasses and shielding cassette therefor, which does not illustrate an eyelid engaging means therein.

While the above-described devices fulfill their respective and particular objects and requirements, they do not describe eyewear in which eyelid engaging means are integrated therein, and which rotate with respect to the eyewear in order to engage and lift eyelids of an end user in order to hold open an eye for installation and/or removal of contact lens with respect to said eye(s); wherein the eyelid engaging eyewear includes an eyewear frame with open spaces in front of the eyes; wherein the eyewear frame includes a suction cup that is centrally located on the eyewear frame and directed inwardly so as to engage forehead skin of an end user in order to secure said eyewear frame there against; wherein the eyelid engaging means attaches to and pivots about a pair of pivot points provided on the eyewear frame; wherein the eyelid engaging means includes armatures that extend laterally at each distal end and which engage eyelids of the end user, and upon rotation of the eyelid engaging means shall lift and hold up the eyelid for use when installing and/or removing contact lens with respect to the eyes of the end user. In this regard, the eyelid-engaging eyewear departs from the conventional concepts and designs of the prior art.

SUMMARY OF THE INVENTION

The eyelid-engaging eyewear is comprised of an eyewear frame having open spaces in front of the eyes and through which eyelid engaging means attach to and pivot. The eyelid engaging means include armatures at distal ends, which engage eyelids of an end user and lift and hold up said eyelids in order to assist in installing and/or removing contact lenses from the eyes of the end user. The eyewear frame includes a centrally located suction cup that is directed inwardly and adheres to the forehead of the end user so as to secure the device to the end user. The eyewear is worn in a normal fashion, and upon rotation of the eyelid engaging means shall lift and hold up said eyelids of the end user.

An object of the invention is to provide an eyelid engaging means that is integrated into the frame of eyewear, and which helps to lift and hold up eyelids of an end user while installing and/or removing contact lenses.

Another object of the invention is to provide an eyewear frame that has open spaces in front of the eyes, and which enables the eyelid engaging means to maneuver there through.

Another object of the invention is to include a suction cup at a middle portion of the eyewear frame, and which is directed inwardly so as to attach to the forehead of the end user thereby adhering the device to the face of the end user.

Another object of the invention is to provide an eyelid engaging means comprised of a pair of armatures extending at distal ends of the eyelid engaging means, which pivots about pivot points located on the eyewear frame.

An even further object of the invention is to form a handle in the eyelid engaging means, which when rotated downwardly shall rotate the armatures, inwardly in order to engage, lift, and hold up the eyelids of the end user.

These together with additional objects, features and advantages of the eyelid-engaging eyewear will be readily apparent to those of ordinary skill in the art upon reading the following detailed description of presently preferred, but nonetheless illustrative, embodiments of the eyelid-engaging eyewear when taken in conjunction with the accompanying drawings.

In this respect, before explaining the current embodiments of the eyelid-engaging eyewear in detail, it is to be understood that the eyelid-engaging eyewear is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the eyelid-engaging eyewear.

It is therefore important that the claims be regarded as including such equivalent construction insofar as they do not depart from the spirit and scope of the eyelid-engaging eyewear. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
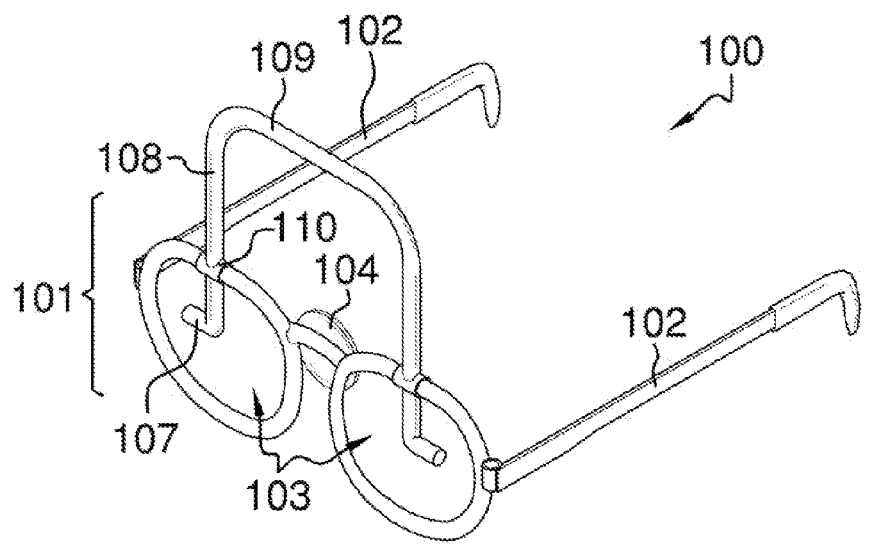
FIG. 1 illustrates a perspective view of the eyelid-engaging eyewear by itself and with the eyelid engaging means vertically oriented.
Figure 2:
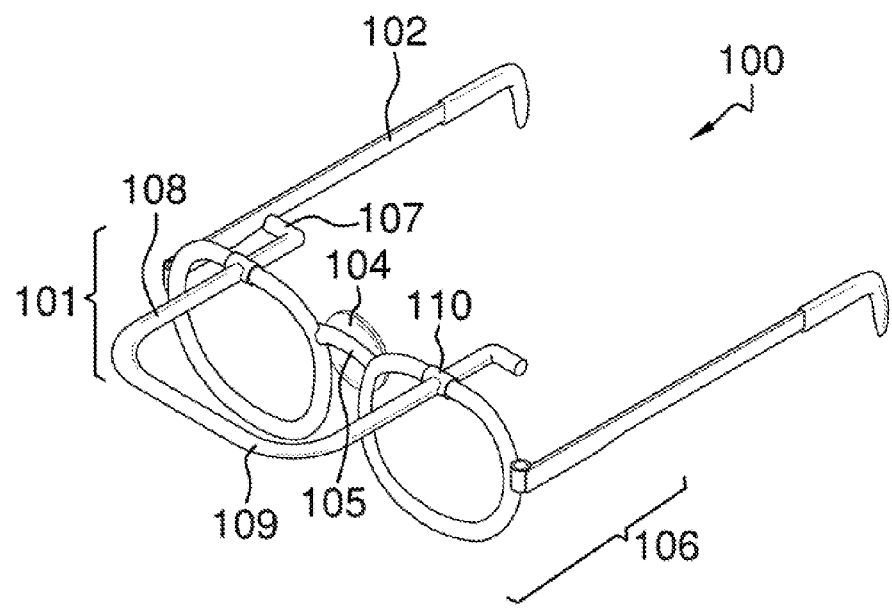
FIG. 2 illustrates a perspective view of the eyelid-engaging eyewear by itself and with the eyelid engaging means horizontally oriented.
Figure 3:
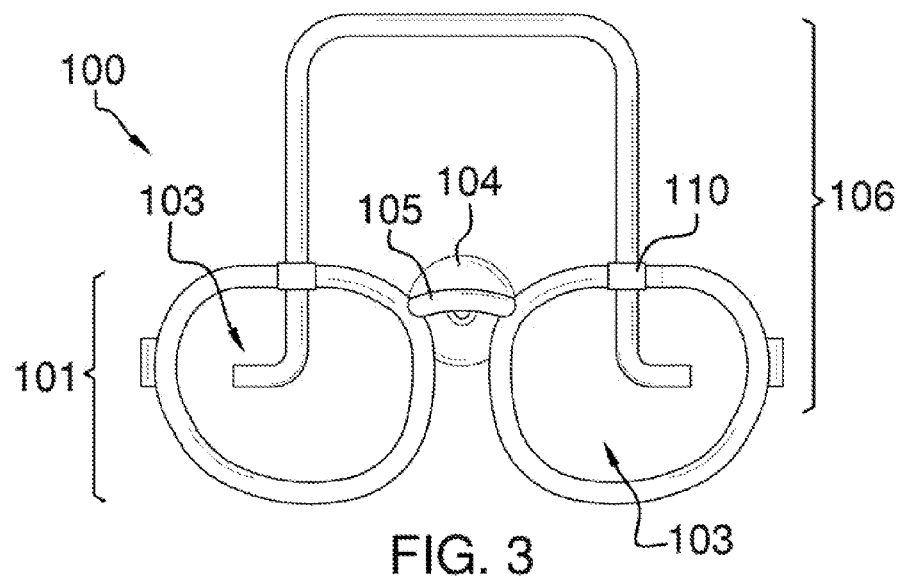
FIG. 3 illustrates a front view of the eyelid-engaging eyewear further defining the location of the suction cup.
Figure 4:
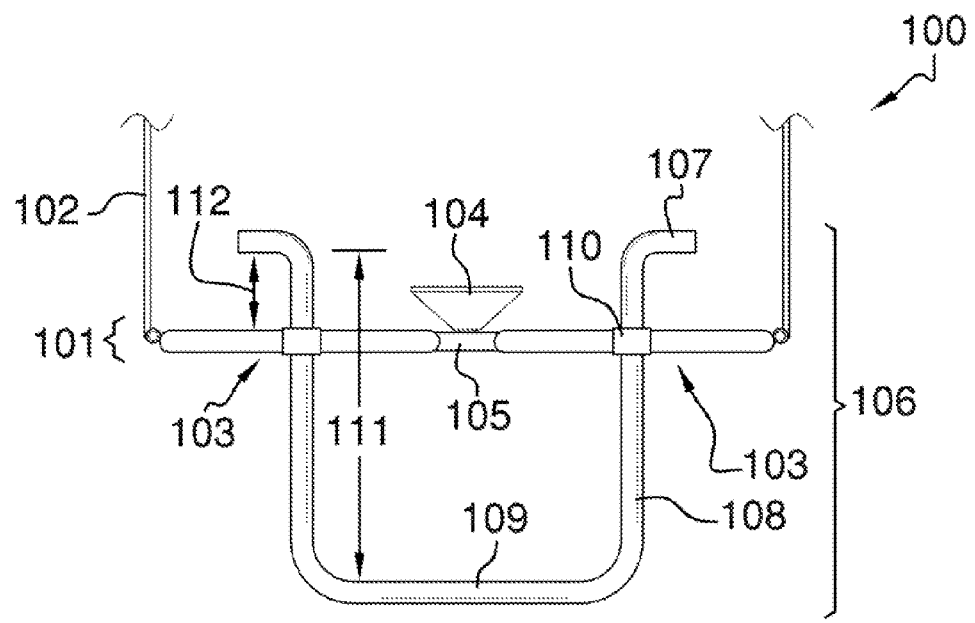
FIG. 4 illustrates a top view of the eyelid-engaging eyewear in which the armatures of the eyelid engaging means are rotated inwardly to the horizontal orientation of FIG. 2.
Figure 5:
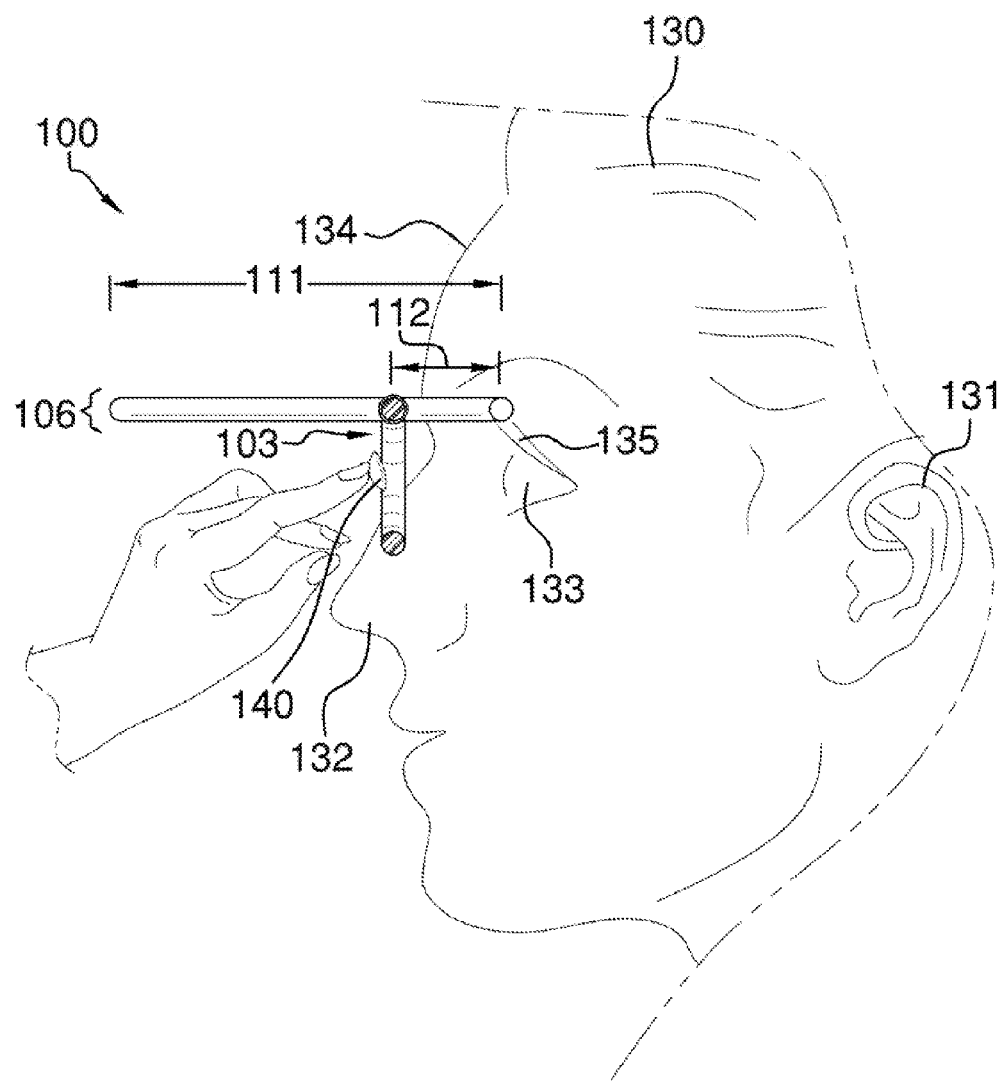
FIG. 5 illustrates a side view of the eyelid-engaging eyewear wherein the eyelid engaging means is rotated horizontally such that the armatures are holding eyelids in an up position while the end user is either removing or installing eye contacts.

Detailed reference will now be made to the preferred embodiment of the present invention, examples of which are illustrated in FIGS. 1-5. An eyelid-engaging eyewear 100 (hereinafter invention) includes an eyewear frame 101 comprised of foldable sides 102, which work in a manner consistent with traditional eyeglasses. Moreover, the foldable sides 102 rotate and engage upon ears 131 of an end user 130 while the eyewear frame 101 rests upon a nose 132 of the end user 130. The eyewear frame 101 is unique to the invention 100 in that open spaces 103 are provided in front of eyes 133 of the end user 130. That being said, in traditional eyeglasses the eyeglass would be located in the open spaces 103.

The eyewear frame 101 includes a suction cup 104 that is positioned at a bridge 105 of the eyewear frame 101. Moreover, the suction cup 104 is directed inwardly, and attaches to a forehead 134 of the end user 130 when the invention 100 is worn thereon. The suction cup 104 is responsible for providing an added level of attachment of the invention 100 onto the end user 130, and further aligns an eyelid engaging means 106 with eyelids 135 of the end user 130.

The eyelid engaging means 106 includes, armatures 107 that extend laterally at distal ends. The eyelid engaging means 106 includes pivoting members 108 that attach to the eyewear frame 101, and rotate there about to maneuver the armatures 107. A handle 109 spans across the pivoting members 108 such that the entire eyelid engaging means 106 resembles a "U" shaped member that rotates at pivot points 110 with the eyewear 101. More specifically, the armatures 107 bend outwardly whereas the handle 109 extends there between. The armatures 107 are separated from the handle 109 by a length 111 of the pivoting members 108.

It shall be noted that the pivoting members 108 rotate about the pivot points 110, and with respect to the eyewear frame 101. Additionally, the pivot points 110 are located at a pivoting distance 112 along the length 111 of the pivoting members 108. Also, the pivoting points 110 are located at a top center position 103A of each of the open spaces 193.

The handle 109 and the armatures 107 are generally parallel with one another. The pivoting members 108 are generally parallel with one another. The pivoting members 108 are generally perpendicular with respect to the handle 109 and the armatures 107.

Use of the eyelid engaging means 106 is relatively simple such that the handle 109 is rotated downwardly and away from the face of the end user 130. The end user 130 shall rotate the eyelid engaging means 106 from a vertical orientation (see FIG. 1) to a horizontal orientation (see FIG. 2). Upon 90 degrees of rotate of the eyelid engaging means from the vertical to the horizontal orientation, the armatures 109 shall engage, lift, and hold up the eyelids 135 of the end user 130. At this point in time, the end user 130 shall either install and/or remove a contact lens 140 with respect to either eye 133 of the end user 130.

It shall be noted that the pivoting distance 112 with respect to the size of the eyewear frame 101 shall dictate how far inwardly the armatures 107 engage.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An eyelid-engaging eyewear comprising:
   wherein an eyewear frame having open spaces configuratively aligned in front of eyes of an end user and about which eyelid engaging member is configured to pivot to engage, lift, and hold up eyelids of an end user so as to aid in installing and/or removing contact lenses with respect to said eyes of the end user;
   wherein the eyewear frame includes foldable sides that rotate and engage upon ears of the end user, and the eyewear frame rests atop of a nose of the end user so as to wear the eyewear frame in a manner consistent with traditional eyeglasses;
   wherein the eyewear frame includes a suction cup at a bridge, and which is directed inwardly so as to adhere to a forehead of said end user;
   wherein the eyelid engaging member includes armatures that extend laterally at distal ends; wherein pivoting members attach to the eyewear frame at pivot points, and rotate there about to maneuver the armatures;
   wherein a handle spans across the pivoting members such that the entire eyelid engaging member resembles a "U" shaped member that rotates at said pivot points with the eyewear frame;
   wherein the handle and the armatures are generally parallel with one another; wherein the pivoting members are generally parallel with one another; wherein the pivoting members are generally perpendicular with respect to the handle and the armatures;
   wherein the armatures bend outwardly whereas the handle extends there between;
   wherein the armatures are separated from the handle by a length of the pivoting members;
   wherein the pivot points are located at a pivoting distance along the length of the pivoting members;
   wherein the pivoting points are located at a top center position of each of the open spaces.

2. The eyelid-engaging eyewear as described in claim 1 wherein the handle rotates from a vertically oriented position, downwardly and away from the face of the end user, during which the armatures rotate inwardly to engage, lift, and hold said eyelids.

3. An eyelid-engaging eyewear comprising:
   wherein an eyewear frame having open spaces configuratively aligned in front of eyes of an end user and about which eyelid engaging member is configured to pivot to engage, lift, and hold up eyelids of an end user so as to aid in installing and/or removing contact lenses with respect to said eyes of the end user;
   wherein the eyewear frame includes foldable sides that rotate and engage upon ears of the end user, and the eyewear frame rests atop of a nose of the end user so as to wear the eyewear frame in a manner consistent with traditional eyeglasses;
   wherein the eyewear frame includes a suction cup at a bridge, and which is directed inwardly so as to adhere to a forehead of said end user;
   wherein the eyelid engaging member includes armatures that extend laterally at distal ends; wherein pivoting members attach to the eyewear frame at pivot points, and rotate there about to maneuver the armatures;
   wherein a handle spans across the pivoting members such that the entire eyelid engaging member resembles a "U" shaped member that rotates at said pivot points with the eyewear frame;
   wherein the handle and the armatures are generally parallel with one another; wherein the pivoting members are generally parallel with one another; wherein the pivoting members are generally perpendicular with respect to the handle and the armatures;
   wherein the armatures bend outwardly whereas the handle extends there between;
   wherein the armatures are separated from the handle by a length of the pivoting members;
   wherein the pivot points are located at a pivoting distance along the length of the pivoting members;
   wherein the pivoting points are located at a top center position of each of the open spaces;
   wherein the handle rotates from a vertically oriented position, downwardly and away from the face of the end user, during which the armatures rotate inwardly to engage, lift, and hold said eyelids.

* * * * *